United States Patent [19]

Logothetis et al.

[11] 4,162,631

[45] Jul. 31, 1979

[54] RARE EARTH OR YTTRIUM, TRANSITION METAL OXIDE THERMISTORS

[75] Inventors: Eleftherios M. Logothetis, Birmingham; Kamlakar R. Laud; John K. Park, both of Ann Arbor, all of Mich.

[73] Assignee: Ford Motor Company, Dearborn, Mich.

[21] Appl. No.: 857,498

[22] Filed: Dec. 5, 1977

[51] Int. Cl.² .......................... G01K 7/18; H01B 1/06
[52] U.S. Cl. .............................. 73/362 AR; 252/521; 338/22 R
[58] Field of Search ............... 73/344, 362 AR, 362.4, 73/362.5; 252/521; 106/73.2; 338/22 R

[56] References Cited

U.S. PATENT DOCUMENTS

| | | | |
|---|---|---|---|
| 3,681,734 | 8/1972 | Brown | 338/28 |
| 3,950,273 | 4/1976 | Jones | 252/521 X |
| 4,010,118 | 3/1977 | Walch | 252/521 |
| 4,010,119 | 3/1977 | Walch | 252/521 |
| 4,010,120 | 3/1977 | Walch | 252/521 |
| 4,010,121 | 3/1977 | Walch | 252/521 |
| 4,010,122 | 3/1977 | Walch | 252/521 |
| 4,013,592 | 3/1977 | Matsuoka et al. | 252/521 |
| 4,014,822 | 3/1977 | Fujikawa | 252/521 X |
| 4,033,906 | 7/1977 | Nagasawa et al. | 252/521 X |
| 4,038,217 | 7/1977 | Nambu et al. | 252/521 |

OTHER PUBLICATIONS

Rao et al., "Electrical Transport in Rare Earth Ortho--Chromites, -Manganites and -Ferrites", Phys. Chem. Solids, vol. 32, pp. 345-358, 1971.

Ganguly et al., "Electron Transport & Magnetic Properties of Rare Earth Ortho-Titanites and -Vanadites, $LnTiO_3$ and $LnVO_3$", Indian Inst. of Tech., 1976.

*Primary Examiner*—Charles Gorenstein
*Attorney, Agent, or Firm*—Edmund C. Ross, Jr.; Olin B. Johnson

[57] ABSTRACT

Thermistors comprising transition metal such as iron, rare earth of the lanthanide series or yttrium, and oxygen exhibit sufficient independence to variation in oxygen partial pressure over a range of exhaust gas conditions of internal combustion engines as to make them particularly suitable for temperature compensation of oxygen sensors such as those derived from titania as well as temperature sensing in other oxygen varying environments.

10 Claims, 4 Drawing Figures

RARE EARTH OR YTTRIUM, TRANSITION METAL OXIDE THERMISTORS

BACKGROUND OF THE INVENTION

This invention relates to thermistor compositions comprising transition metal such as iron, rare earth of the lanthanide series or yttrium and oxygen, including, in particular, thermistors that operate free of significant oxygen dependence, especially in the exhaust gas of internal combustion engines and, accordingly, are suited for use with oxygen sensors such as those derived from titania.

The use of oxygen sensors containing titania that are temperature compensated by a separate chip is illustrated in commonly assigned Ser. No. 839,704 (Temperature Compensated Resistive Exhaust Gas Sensor Construction) filed in name of Cermak et al. on Oct. 5, 1977, which is hereby incorporated herein by reference, especially including those portions comprehending the use of oxygen sensors and thermal compensators therefor in feedback fuel control systems of internal combustion engines. Previous suggestions for providing such temperature compensation at least partially independent of oxygen partial pressure, made, for example, in the next above application, include densifying a ceramic as titania (see, also, commonly assigned Ser. No. 839,700 (Titania Thermistor and Method for Fabricating) filed in name of Merchant et al. on Oct. 5, 1977) so as to minimize response to oxygen changes under exhaust gas conditions as well as a suggestion of coating a ceramic with, for example, glass (see, also, commonly assigned Ser. No. 839,705 (Encapsulated Titania Thermistor and Method of Fabrication) filed in name of Heiney et al. on Oct. 5, 1977) so as to provide a barrier to oxygen.

THE INVENTION

Figure 1:
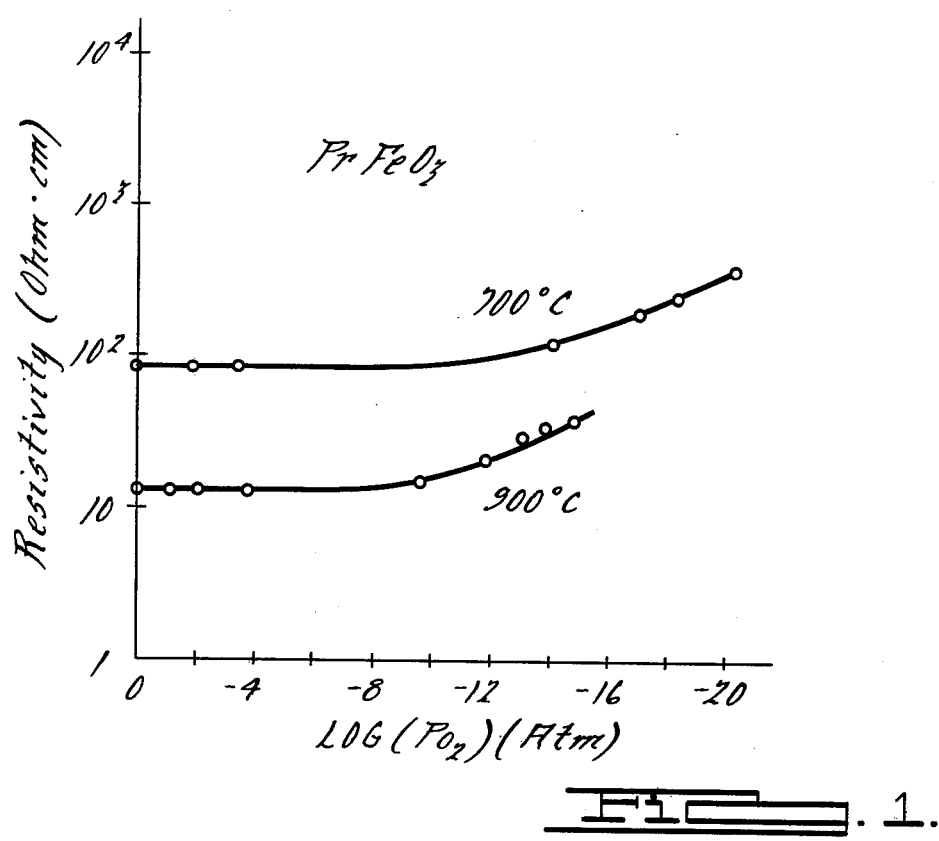
FIG. 1 illustrates dependence of resistivity of $PrFeO_3$ thermistor on oxygen partial pressure for two temperatures.

Rare earth compositions compising ions of transition metal such as iron, rare earth of the lanthanide series or yttrium, and oxygen in a respective molar ratio of about 1:1:3 provide temperature compensation while not being significantly affected by variation in oxygen partial pressure under internal combustion engine, such as automotive, exhaust gas conditions. Preferred thermistor compositions comprising praseodymium as the rare earth have the advantage of activation energies comparable to oxygen sensors derived from titania making them especially suitable for use therewith.

DETAILED DESCRIPTION OF THE INVENTION

Thermistor compositions of this invention can be prepared, for example, by heating a mixture of rare earth oxide such as $Pr_6O_{11}$ and $Fe_2O_3$ at temperatures above 1000° C., preferably in a range of about 1250°–1450° C., so as to provide compounds corresponding to the formula $RFeO_3$ wherein R is, for example, praseodymium or other rare earth of the lanthanide series or yttrium or compatible mixtures of any of these, preferably all or essentially all single phase. Preferred ceramics can then be made by any suitable process, such as by casting a tape or die pressing into green body shape (e.g., chip, pellet) and sintering at temperatures also above 1000° C., preferably in a range of about 1300°–1500° C., to provide compositions with densities currently preferred in a range such as between about 60 and 95% of theoretical. Density, however, is not a critical factor for attaining desired performance of the thermistor in environments such as automotive exhaust gas.

Other methods in the preparation of thermistor compositions of this invention include, rather than heating of the mixed oxides, heating of mixed salts as, for example, by dissolving the separate oxides in stoichiometric ratio (i.e., rare earth or yttrium to iron of about 1:1 gram atom ratio) in hydrochloric acid, evaporating the water, heating slowly to high temperature, e.g., 600° C., followed by sintering at still higher temperature, e.g., 1400° C. Alternatively, the rare earth oxide or yttrium oxide can be dissolved in such stoichiometric ratio with iron in nitric acid followed by evaporating and heating as above.

The thermistors suitable for employment in feedback fuel control systems are conveniently made during the above noted chip or pellet forming processes by including during, for instance, the die pressing operation spaced apart conducting leads such as platinum wires which then serve as electrical connection means for communicating the thermistor to the other circuit elements of the feedback fuel control system. A preferred arrangement of oxygen sensor, thermistor and other circuit elements is identified in the above-noted Ser. No. 839,704 (Temperature Compensated Resistive Exhaust Gas Sensor Construction) filed in name of Cermak et al., on Oct. 5, 1977, which illustrates preferred circuit arrangement. Such arrangement includes a series electrical connection between the oxygen sensor (e.g., titania) and thermistor such that when a reference voltage is applied across the series connection, the voltage signal taken at the midpoint between the chips is representative of the oxygen partial pressure independent of temperature. Although electrical arrangement of the oxygen sensor, thermistor and other elements may be made otherwise, such series connection advantageously allows for use of a constant voltage source input to provide a variable voltage signal output. Of course, the thermistors herein may be used alone, if desired, to sense temperature in oxygen varying environments or with sensors that monitor other gases.

Preferred praseodymium containing compounds corresponding to $PrFeO_3$ as wherein the molar ratio is, respectively, about 1:1:3, have particular advantage over certain other rare earth compositions when used as temperature compensators for titania oxygen gas sensors such as those disclosed in U.S. Pat. No. 3,886,785 and, particularly, as thermistors to replace the thermistors disclosed in commonly assigned Ser. No. 839,706 (Thermistor Temperature Conpensated Titania Exhaust Gas Sensor) filed in name of McDonald on Oct. 5, 1977, which is hereby incorporated herein by reference. This advantage derives from the fact that such thermistor compositions comprising praseodymium can have activation energies that are comparable to titania activation energies at temperatures which correspond to those in a range seen in exhaust gas of internal combustion engines.

The thermistors of this invention may be fabricated in pellet form as beads, discs, cylinders etc. and, as previously mentioned, comprise electrically conducting leads or contacts as platinum wire that are preferably pressed into the thermistor composition during,, for instance, shaping operations or, alternatively, connected in other fashion such as with platinum or other conducting paste. One suggested method for fabrication on a large scale the thermistors herein is like that disclosed in U.S. Pat. No. 3,886,785.

As previously indicated, the thermistor compositions herein exhibit such insensitivity to oxygen partial pressure as to minimize necessity of special treatment to provide such oxygen insensitivity, although, however, such treatment is not precluded as, for example, coating to increase life of the thermistor.

It is anticipated that other transition metals such as cobalt and manganese can be used alone, or together, with, or in place of iron in thermistor compositions of this invention, especially those comprising a compound corresponding to the formula $RFeO_3$, wherein R is as hereinbefore defined, and, particularly, if R comprises preferred praseodymium, to provide not only temperature compensation that is not significantly dependent on oxygen partial pressure but also desirable activation energies that are compatible with sensors such as those derived from titania.

EXAMPLE 1

The compound $PrFeO_3$ was prepared by calcining a mixture of $Pr_6O_{11}$ (99.9% purity, obtained from Research Chemical) and $Fe_2O_3$ (99.9% purity obtained from Research Chemical) at 1350° C. for 1 hour, followed by grinding under acetone and subsequent heating at 1350° C. for 6 hours.

For the electrical measurements, ceramic specimens were prepared in the form of cylindrical pellets, 3 mm in diameter and 1 cm long, by die-pressing without binder and sintering in alumina boats at 1400° C. for 1 hour. The electrical resistivity was measured by a 4-probe technique. Electrical connections to the specimen were made by attaching platinum wires with platinum paste. The specimens were mounted inside a quartz vessel that was placed in a furnace. The oxygen partial pressure ($P_{O_2}$) on the ambient atmosphere was established by various gas mixtures: $O_2/CO_2$ mixtures for $P_{O_2} > 10^{-6}$ atm and $CO/CO_2$ mixtures for $P_{O_2} < 10^{-6}$ atm.

Figure 2:
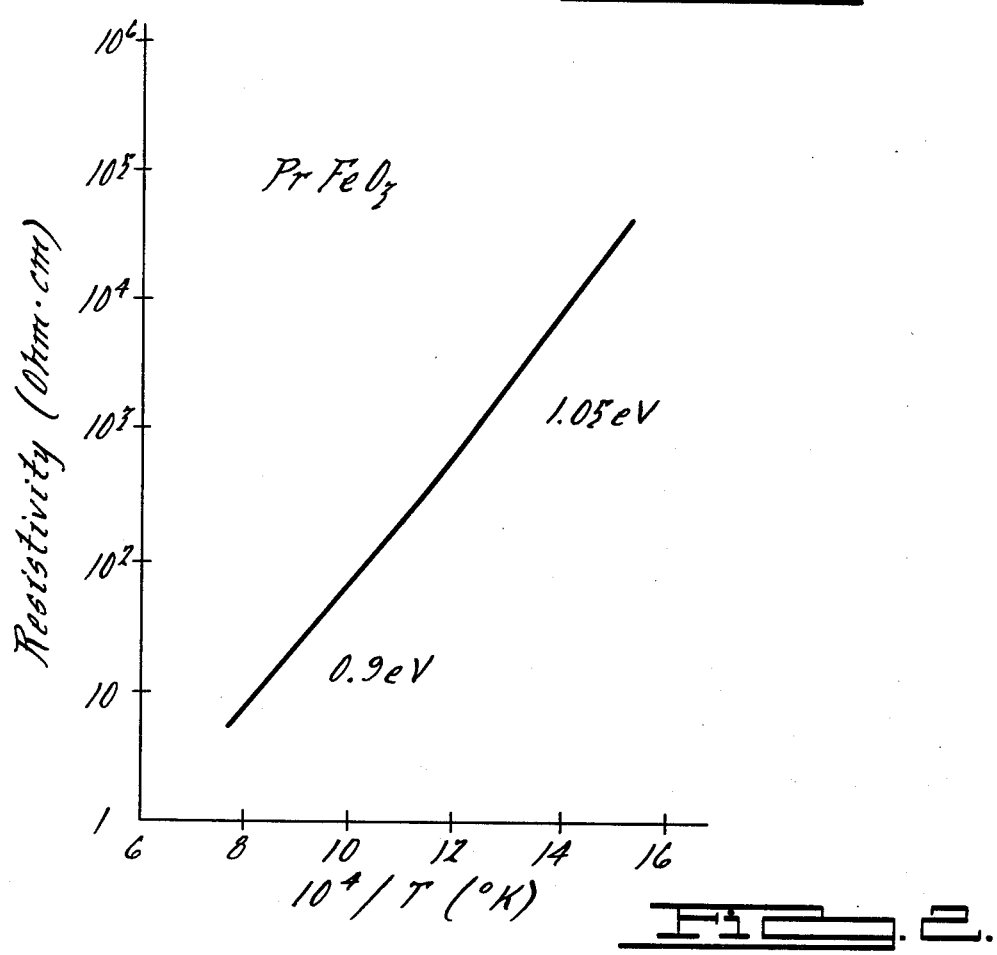
FIG. 2 illustrates dependence of resistivity in pure oxygen of $PrFeO_3$ thermistor on the reciprocal of absolute temperature.

FIG. 1 shows the dependence of the electrical resistivity of $PrFeO_3$ in the ambient $P_{O_2}$ at two temperatures, 700° and 900° C. FIG. 2 shows the temperature dependence of the resistivity in a pure oxygen environment. The resistivity was calculated from the measured specimen resistance and geometrical dimensions without correcting for the porosity of the specimen. It is expected that for specimens with densities higher than about 80% of theoretical, the uncorrected value of resistivity is larger than the true value by a factor of about not more than 1.5.

The resistivity of $PrFeO_3$ is independent of changes in $P_{O_2}$ at high $P_{O_2}$ ($P_{O_2} > 10^{-4} - 10^{-6}$ atm) and increases slowly with decreasing $P_{O_2}$ for low $P_{O_2}$. The resistivity of $PrFeO_3$ decreasees with increasing temperature with an activation energy of about 1.0 eV. A small break in the log vs 1/T curve is observed at 620° C.

Figure 3:
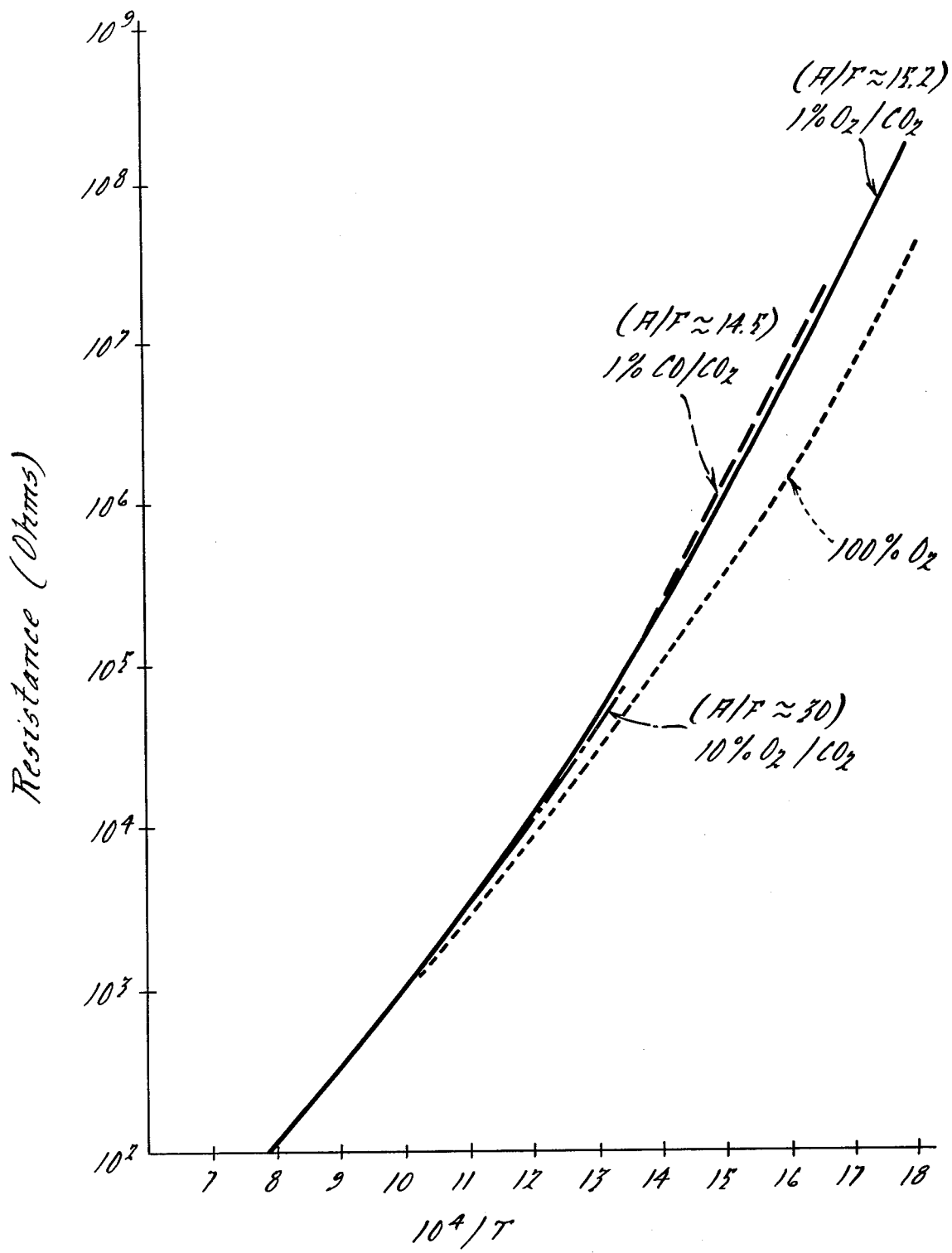
FIG. 3 illustrates the resistance of a $PrFeO_3$ thermistor in environments with different oxygen partial pressures (different simulated A/F (air/fuel) ratios) against the reciprocal of absolute temperature.

FIG. 3, derived from tests employing differing oxygen partial pressure environments corresponding to simulated air fuel (A/F) ratios that are seen in automotive exhaust gas further illustrates the insensitivity of the $PrFeO_3$ thermistor to oxygen partial pressure. The A/F ratios were simulated with mixed gases as described above.

EXAMPLE 2

Figure 4:
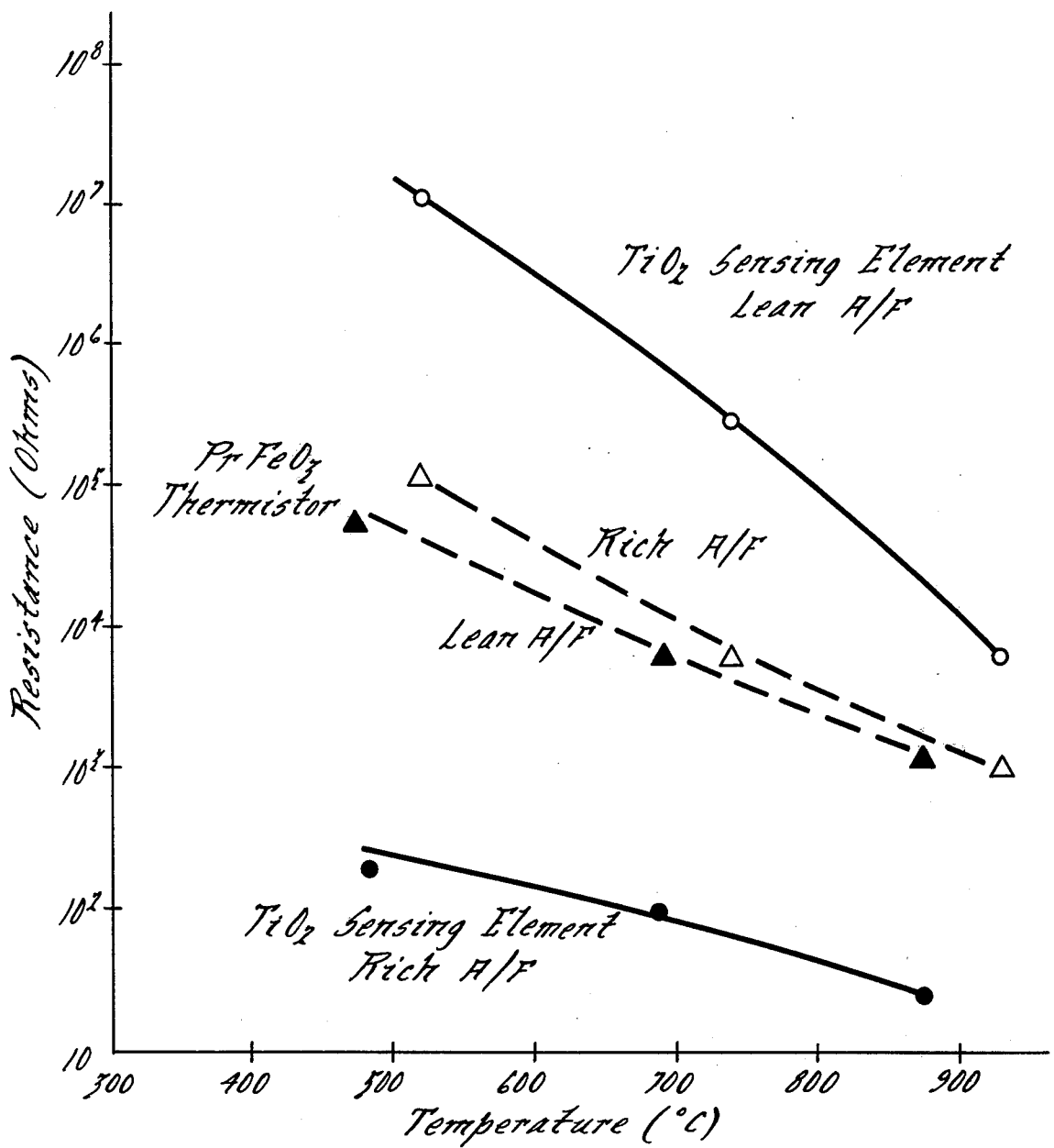
FIG. 4 illustrates the resistance of a $PrFeO_3$ thermistor and a titania oxygen sensor element in lean and rich simulated A/F ratio environments against temperature.

A simulated exhaust gas environment using a propane burner is used to obtain resistance in ohms as a function of temperature for a $PrFeO_3$ thermistor element, preferred as described in Example 1 and a titania oxygen sensing element prepared generally in accordance with the method described in Ser. No. 839,701 filed Oct. 5, 1977 by Esper et al. and entitled "Catalytic Material Impregnated, Porous Variably Resistive Exhaust Gas Sensor and Method of Fabrication", which is herein incorporated by reference for its teaching of manufacture. FIG. 4 shows the results.

As can be seen, resistance changes of the two elements with temperature can be made to match and the oxygen dependence of the thermistor is negligibly small compared to the titania element. For these tests, the simulated exhaust was obtained with a propane burner and the measurement of resistances of titania and thermistor elements was made by conventional techniques.

What is claimed is:

1. A method of sensing temperature in an oxygen varying environment that contains combustion engine exhaust gas which comprises exposing to the environment a thermistor composition comprising (a) transition metal comprising iron, (b) one or more rare earth of the lanthanide series or yttrium and (c) oxygen in a respective molar ratio of the ions of about 1:1:3 and detecting its resistance.

2. A method in accordance with claim 1, wherein the rare earth comprises praseodymium.

3. A method in accordance with claim 1, wherein the thermistor composition comprises a compound having a formula corresponding to $RFeO_3$ wherein R is rare earth of the lanthanide series or yttrium.

4. A method in accordance with claim 3, wherein the compound comprises a single phase having a density higher than about 60% of theoretical.

5. A method in accordance with claim 4, wherein the rare earth comprises praseodymium.

6. In an automotive feedback fuel control system that utilizes an oxygen sensor comprising titania and a thermistor in series electrical connection therewith for temperature compensation of the oxygen sensor, the improvement wherein the thermistor comprises a compound having a formula corresponding to $PrFeO_3$.

7. A method of sensing temperature in an oxygen varying environment which comprises exposing to the environment a thermistor composition comprising a compound having a formula corresponding to $RFeO_3$ wherein R is a rare earth of the lanthanide series or yttrium, the thermistor composition being in electrical communication with an oxygen sensor comprising titania, and detecting resistance of the thermistor composition.

8. A method in accordance with claim 7 wherein the thermistor composition comprises a compound having a formula corresponding to $PrFeO_3$.

9. A method in accordance with claim 7 wherein the thermistor composition comprises a compound having a formula corresponding to $PrFeO_3$.

10. A method of sensing temperature in an oxygen varying environment that contains combustion engine exhaust gas which comprises exposing to the environment a thermistor composition comprising a compound having a formula corresponding to $RFeO_3$ wherein R is a rare earth of the lanthanide series or yttrium, the thermistor composition being used in combination with an oxygen sensor and detecting resistance of the thermistor composition.

* * * * *

UNITED STATES PATENT AND TRADEMARK OFFICE
CERTIFICATE OF CORRECTION

PATENT NO. : 4,162,631
DATED : July 31, 1979
INVENTOR(S) : Eleftherios M. Logothetis et al It is certified that error appears in the above-identified patent and that said Letters Patent are hereby corrected as shown below:

Delete Columns 5 and 6 and insert therefore:

9. A method of sensing temperature in an oxygen varying environment that contains combustion engine exhaust gas which comprises exposing to the environment a thermistor composition comprising a compound having a formula corresponding to $RFeO_3$ wherein R is a rare earth of the lanthanide series or yttrium, the thermistor composition being used in combination with an oxygen sensor and detecting resistance of the thermistor composition.

10. A method in accordance with claim 9 wherein the thermistor composition comprises a compound having a formula corresponding to $PrFeO_3$.

Signed and Sealed this

Thirtieth Day of October 1979

[SEAL]

Attest:

RUTH C. MASON
Attesting Officer

LUTRELLE F. PARKER
Acting Commissioner of Patents and Trademarks